United States Patent [19]

Kawashima et al.

[11] Patent Number: 5,736,546

[45] Date of Patent: Apr. 7, 1998

[54] 1,4-(DIPHENLYALKYL) PIPERAZINE DERIVATIVES

[75] Inventors: Yoichi Kawashima, Kyoto; Junzo Matsumoto, Ashiya; Kiyoshi Matsuno, Toyonaka; Toshihiko Senda, Kishiwada; Keiko Hirano, Nara, all of Japan

[73] Assignee: Santen Pharmaceutical Co., Ltd., Osaka, Japan

[21] Appl. No.: 586,661

[22] PCT Filed: Jul. 25, 1994

[86] PCT No.: PCT/JP94/01220

§ 371 Date: Mar. 25, 1996

§ 102(e) Date: Mar. 25, 1996

[87] PCT Pub. No.: WO95/04050

PCT Pub. Date: Feb. 9, 1995

[30] Foreign Application Priority Data

Jul. 28, 1993 [JP] Japan .................. 5-185839

[51] Int. Cl.$^6$ .................. C07D 295/096; A61K 31/495
[52] U.S. Cl. .................. 514/255; 544/398
[58] Field of Search .................. 544/398; 514/255

[56] References Cited

U.S. PATENT DOCUMENTS

| | | | |
|---|---|---|---|
| 4,574,156 | 3/1986 | Morita et al. | 544/398 |
| 5,281,598 | 1/1994 | Van Bakel et al. | 544/398 |
| 5,389,630 | 2/1995 | Sato et al. | 544/398 |
| 5,428,037 | 6/1995 | Pascal et al. | 514/252 |

FOREIGN PATENT DOCUMENTS

| | | | |
|---|---|---|---|
| 55-83771 | 6/1980 | Japan . | |
| 61-33827 | 8/1986 | Japan . | |
| WO 91/09594 | 7/1991 | WIPO . | |
| 9424116 | 10/1994 | WIPO | 544/398 |

OTHER PUBLICATIONS

Kanebo, Chemical Abstracts, vol. 94, No. 121583 (1981) (Abstract for JP 80 83,771, Jun. 24, 1980).

Surendra Bahadur et al, "Synthesis of Some New Mannich Bases of N-(4-Hydroxy-3-methoxy-benzylidene)-4-methoxy benzoic acid hydrazide as Potential Biologically Active Agents", J. Indian Chem. Soc., vol. LVII, Sep. 1980, pp. 918-919.

H.W. Kosterlitz et al, "Effects of Changes in the Structure of Enkephalins and of Narcotic Analgesic Drugs on Their Interactions with μ- and δ-Receptors", Br. J. Pharmac. (1980), 68, pp. 333-342.

Toshitaka Nabeshima, "Involvement of Different Opioid Receptor Subtypes in Electric Shock-Induced Analgesia and Motor Suppression in the Rat", European Journal of Pharmacology, 114 (1985) pp. 197-207.

William A. Pulsinelli et al, "A New Model of Bilateral Hemispheric Ischemia in the Unanesthetized Rat", Stroke, vol. 10, No. 3, May-Jun. 1979, pp. 267-272.

Diane L. DeHaven-Hudkins et al, "Characterization of the binding of [$^3$H] (+)-pentazocine to σ recognition sites in guinea pig brain", European Journal of Pharmacology—Molecular Pharmacology Section, 227 (1992), pp. 371-378.

Kiyoshi Matsuno et al, "Correlation between potentiation of neurogenic twitch contraction and benzomorphan σ receptor binding potency in the mouse vas deferens", European Journal of Pharmacology, 231 (1993), pp. 451-457.

Kiyoshi Matsuno et al, "Increase of extracellular acetylcholine level in rat frontal cortex induced by (+)N-allynormetazocine as measured by brain microdialysis", Brain Research, 575 (1992), pp. 315-319.

William Koopmans Summers et al, "Oral Tetrahydroaminoacridine in Long-Term Treatment of Senile Dementia, Alzheimer Type", The New England Journal of Medicine, vol. 315, No. 20, Nov. 13, 1986, pp. 1241-1245.

X. Pascaud et al, "Effect of Selective Signa Ligands on Duodenal Alkaline Secretion in the Rat", The Journal of Pharmacology and Experimental Therapeutics, vol. 255, No. 3, 1990, pp. 1354-1359.

Tsung-Ping Su, "σ receptors, Purative links between nervous, endocrine and immune systems", Eur. J. Biochem. 200, (1991), pp. 633-642.

Solomon H. Snyder et al, "Receptor Mechanisms in Anti-psychotic Drug Action: Focus on Sigma Receptors", Journal of Neuropsychiatry, vol. 1, No. 1, Winter 1989, pp. 7-15.

Michael W. Majchrzak et al, "Synthesis and Action on the Central Nervous System of Mescaline Analogues Containing Piperazine or Homopiperazine Rings", Journal of Pharmaceutical Sciences, vol. 72, No. 3, Mar. 1983, pp. 304-306.

S. William Tam, "Naloxone-inaccessible σ receptor in rat central nervous system", Proc. Natl. Acad. Sci. USA, vol. 80, Nov. 1983, pp. 6703-6707.

K. Lanyi et al, "Piperazin-Derivative", Pharmazie (1970) 29, pp. 189-193.

Yasumatsu et al Folia Pharmacol. Japan, 90, (1987), pp. 321-330.

*Primary Examiner*—Emily Bernhardt
*Attorney, Agent, or Firm*—Frishauf, Holtz, Goodman, Langer & Chick, P.C.

[57] ABSTRACT

This invention relates to novel compounds of the formula [I],

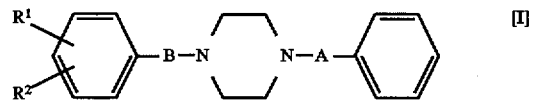

wherein $R^1$ and $R^2$ are the same or different and each represents a lower alkoxy group; A and B are the same or different and each represents a lower alkylene group.

The compounds of this invention have affinities for sigma receptors and are useful for therapeutic agents for cerebral neural function disorders such as dementia, depression, schizophrenia and anxiety neurosis, diseases accompanying abnormal immune response and cryptorrhea, digestive ulcer, etc.

22 Claims, No Drawings

1,4-(DIPHENLYALKYL) PIPERAZINE DERIVATIVES

TECHNICAL FIELD

The present invention relates to novel 1,4-(diphenylalkyl) piperazine derivatives which have affinities for sigma receptors and are useful for therapeutic agents for cerebral neural function disorders such as dementia, depression, schizophrenia and anxiety neurosis, diseases accompanying abnormal immune response and cryptorrhea, digestive ulcer, etc.

BACKGROUND ART

Many studies on sigma receptors have recently been made, and it has been found out that compounds having high affinities for the sigma receptor are useful for therapeutic agents for cerebral neural function disorders such as dementia, depression, schizophrenia and anxiety neurosis, diseases accompanying abnormal immune response and cryptorrhea, digestive ulcer, etc. (Journal of Neuropsychiatry, 1, 7–15 (1989); Eur. J. Biochem., 200, 633–642 (1991); J. Pharmacol. Exp. Ther., 255, 1354–1359 (1990)).

On the other hand, 1,4-(diphenylalkyl)piperazine derivatives are reported to have affinities for sigma receptors (WO91/09594). However, this report mainly relates to the compounds which have no substituents at a phenyl ring, and it does not recite studies about influence on affinities for sigma receptors by introducing substituents into the phenyl ring.

The following prior arts disclose compounds whose chemical structures are similar to those of the compounds of this invention, though different from this invention in objects, actions and effects. Many 1,4-(diphenylalkyl) piperazine derivatives having no substituents at both of two phenyl rings and having substituents at both of two phenyl rings have already been synthesized (Chem. Ber., 100, 3045 (1967); J. Pharm. Sci., 72, 304 (1983)). However, there are few reports of research about 1,4-(diphenylalkyl)piperazine derivatives having substituents at only one phenyl ring and having no substituents at the other phenyl ring.

For example, only a compound wherein the 3rd-position of the phenyl ring is substituted by methoxy group and the 2nd-position is substituted by hydroxyl group (Pharmazie, 29, 189 (1970)) and a compound wherein the 2nd-, 3rd- and 4th-positions of one phenyl ring are substituted by methoxy groups (Japanese Patent Laid-open Publication No. 55-83771) are reported as compounds wherein one phenyl ring has no substituents and the other phenyl ring has alkoxy groups. Of course, affinities for sigma receptors have not been reported about these compounds.

It has not been studied yet how affinities for sigma receptors vary by introducing substituents into the phenyl ring of 1,4-(diphenylalkyl)piperazine derivatives, and it was an important subject to find a compound having a high affinity for sigma receptors by introducing substituents into the phenyl ring.

In addition, it has not been studied fully to introduce at least one substituent into only one phenyl ring of 1,4-(diphenylalkyl)piperazine derivatives, and it was an interesting subject to synthesize and study such compounds.

The inventors synthesized novel 1,4-(diphenylalkyl) piperazine derivatives having specific substituents at only one phenyl ring and examined effects of the compounds on sigma receptors. As the result of the examination, compounds having two alkoxy groups at only one phenyl ring were found to have high affinities for sigma receptors.

Furthermore it was found that these compounds have not only high affinities for sigma receptors but also improving effects on learning disorder due to cerebrovascular disorder and increasing effects on the amount of intracerebral acetylcholine, and that the compounds are particularly useful for therapeutic agents for cerebral neural function disorders.

SUMMARY OF THE INVENTION

This invention relates to the compounds represented by following formula [I], salts thereof (hereinafter referred to as "the compounds of this invention") and therapeutic agents for cerebral neural function disorders which comprise them as active ingredients:

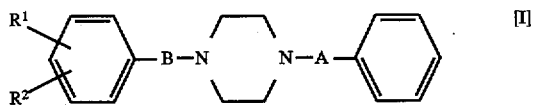

wherein, $R^1$ and $R^2$ are the same or different and each represents a lower alkoxy group; "A" and "B" are the same or different and each represents a lower alkylene group.

The same definition is applied hereinafter.

DETAILED DESCRIPTION OF THE INVENTION

The terms defined above are explained as follows in more detail;

The term "lower alkoxy" stands for straight or branched alkoxy having 1 to 6 carbon atoms exemplified by methoxy, ethoxy, propoxy, isopropoxy, t-butoxy and hexyloxy.

The term "lower alkylene" stands for straight or branched alkylene having 1 to 6 carbon atoms exemplified by methylene, ethylene, propylene, butylene, (dimethyl)methylene and (diethyl)methylene.

The salts of the compound of this invention are pharmaceutically acceptable salts such as hydrochloride, sulfate, maleate and fumarate.

Preferred examples of the groups defined above are explained as follows in detail.

Preferred examples of the lower alkylene groups "A" and "B" are straight alkylene group(s) having 2 to 4 carbon atoms, that is, ethylene, propylene and/or butylene. Preferred examples of the combination of "A" and "B" are shown below;

"A" is propylene and "B" is ethylene, both "A" and "B" are propylene, both "A" and "B" are ethylene, "A" is butylene and "B" is ethylene.

Particularly preferred examples of the combination of "A" and "B" are shown below;

"A" is propylene and "B" is ethylene, both "A" and "B" are propylene.

Each of $R^1$ and $R^2$ is preferably a methoxy group. In particular, a compound wherein methoxy groups substitute at vicinal positions in one phenyl ring is preferable. The most preferred example is a compound wherein methoxy groups substitute at the 3rd- and 4th-positions respectively.

Preferred examples of practical compounds are 1-[2-(3,4-dimethoxyphenyl)ethyl]-4-(3-phenylpropyl)piperazine, 1-[2-(3,4-dimethoxyphenyl)ethyl]-4-(2-phenylethyl)piperazine, 1-[2-(3,4-dimethoxyphenyl)ethyl]-4-(4-phenylbutyl)piperazine, 1-[3-(3,4-dimethoxyphenyl)propyl]-4-(3-phenylpropyl)piperazine, or salts thereof.

Particularly preferred examples of compounds are 1-[2-(3,4-dimethoxyphenyl)ethyl]-4-(3-phenylpropyl)piperazine, 1-[3-(3,4-dimethoxyphenyl)propyl]-4-(3-phenylpropyl)piperazine, or salts thereof.

Typical synthetic methods for preparing the compounds of this invention are shown in the following reaction schemes 1) and 2).

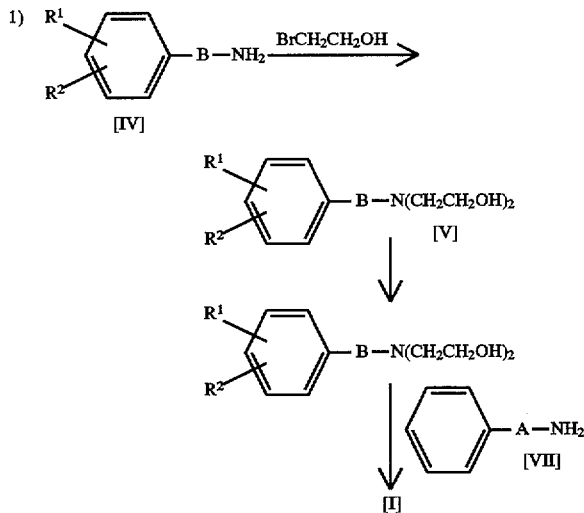

wherein X is halogen or a reactive group exemplified by a lower alkanesulfonyloxy group. The same definition applies to the reaction below.

In this method, the compound of the formula [V] is prepared by reacting the compound of the formula [IV] with 2-bromoethanol. The compound of the formula [V] is reacted with thionyl chloride, methanesulfonyl chloride, etc. to give the compound of the formula [VI], which is then reacted with the amine derivative of the formula [VII] to give the compound of this invention represented by the formula [I].

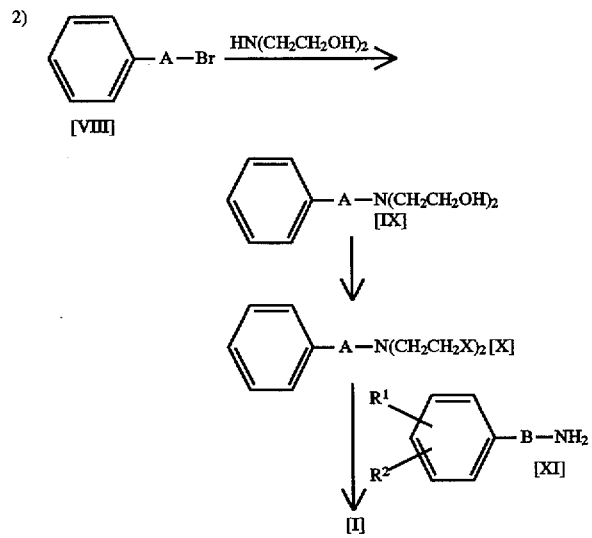

In this method, the reaction order of method 1) is reversed, and reaction conditions, etc. are the same as those of method 1).

The compounds prepared by the above methods can be converted into their salts as previously mentioned by conventional method.

Some of the compounds of the formula [I] have optical isomers, and these isomers are also included in this invention.

In order to study the utility of the compounds of this invention, an experiment was performed to examine affinities of the compounds for sigma receptors. Details are shown in the article of Pharmacological Test described later in this specification. The inventors examined affinities of the compounds for sigma receptors using [$^3$H](+)-SKF-10047 or [$^3$H](+)-PTZ as labeled ligands. As the result of the examination, the compounds of this invention were found to exhibit high affinities for sigma receptors.

Since compounds increasing the amount of intracerebral acetylcholine are reported to be useful for therapeutic agents for dementia, etc. (The New England Journal of Medicine, 315, 1241-1245 (1986)), the amount of acetylcholine in rat brain was then measured according to the report of Matsuno et al. (Brain Research, 575, 315-319 (1992)). As the result of the measurement, the compounds of this invention were found to exhibit increasing effects on the amount of acetylcholine.

In addition, an experiment was performed using learning disorder models caused by ischemia known as disease models of dementia caused by cerebrovascular disorder, that is, rats in transient ischemic condition by blockading artery according to the method of Pulsinelli et al. (Stroke, 10, 267 (1979)). Evaluating the result of the experiment according to the method of Yasumatsu et al, (Folia Pharmacologica Japonica, 90, 321 (1987)), the compounds of this invention were found to have improving effects on learning disorders.

From the results of the above pharmacological tests, it was found that the compounds of this invention have high affinities for sigma receptors and that the compounds have wide pharmaceutical uses for therapeutic agents for diseases in which sigma receptors are concerned, for example, cerebral neural function disorders such as dementia, depression, schizophrenia and anxiety neurosis, diseases accompanying abnormal immune response and cryptorrhea, digestive ulcer, etc. It was also found that the compounds have increasing effects on the amount of intracerebral acetylcholine and improving effects on learning disorders due to cerebrovascular disorder. From these findings, the compounds were proved to be particularly useful for therapeutic agents for cerebral neural function disorders.

By the way, certain piperazine derivatives are reported to have a morphine-like physical dependence (Examined Japanese Patent Publication No. 61-33827). Such effect is not favorable for medicaments. Accordingly, an experiment was performed to examine whether the compounds of this invention exhibit morphine-like effects. A compound having the morphine-like effect is known to have a high affinity for µ receptors, and if the affinity for µ receptors is low, the morphine-like effect of the compound is judged to be also low. Affinities of the compounds of this invention for µ receptors were examined using [$^3$H]DAMGO as a labeled ligand. As the result of the examination, it was found that affinities of the compounds of this invention for µ receptors are low and that the compounds substantially exhibit no morphine-like effects.

In order to apply one compound to a medicament, it is preferable that the difference between the amount for exhibiting effect and the amount for exhibiting side-effect is large. That is to say, it is preferable that the affinity for sigma receptors is high and the affinity for µ receptors is low in this invention, and the experimental results described later demonstrate that the compounds of this invention are excellent as medicaments.

The compounds of this invention can be administered orally or parenterally. Examples of dosage forms are tablet, capsule, soft capsule, granule, injection, etc. The preparations can be formulated by the conventional methods. For example, oral preparations such as a tablet, a capsule, a soft capsule and granule can be produced, if necessary, by adding diluents such as lactose, starch, crystalline cellulose or vegetable oil; lubricants such as magnesium stearate or talc; binders such as hydroxypropylcellulose or polyvinyl pyrrolidone; a disintegrator such as calcium carboxymethylcellulose; coating agents such as hydroxypropylmethylcellulose, macrogol or silicone resin; or a film forming agent such as gelatin coat. The dosage is adjusted depending on symptoms, dosage form, etc., but the usual daily dosage is 1 to 1000 mg, which can be given in one or a few divided doses.

THE BEST EMBODIMENT OF THE INVENTION

Reference Examples (Preparation of Intermediates)

Reference Example 1

N,N-Bis(2-hydroxyethyl)-2-(3,4-dimethoxyphenyl) ethylamine (reference compound No. 1-1)

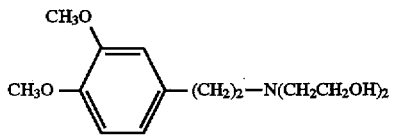

To a solution of 2-(3,4-dimethoxyphenyl)ethylamine (20 g) and 2-bromoethanol (73.4 g) in ethanol (250 ml) was added potassium carbonate (50.2 g). The mixture was refluxed for 24 hours. The insoluble matter was filtered out, the filtrate was concentrated in vacuo, and chloroform (300 ml) was added to the concentrate. This solution was washed with a 10% aqueous solution of sodium bicarbonate and a saturated sodium chloride solution, dried over anhydrous sodium sulfate, and concentrated in vacuo. The oily residue was purified by silica gel column chromatography to give 13.5 g (46%) of the titled compound.

IR (film, $cm^{-1}$) 3383, 2941, 1516, 1464, 1262, 1236, 1142, 1029

The following compound was prepared in the similar manner to Reference Example 1.
N,N-Bis(2-hydroxyethyl)-3-(3,4-dimethoxyphenyl) propylamine (reference compound No. 1-2)

IR (film, $cm^{-1}$) 3386, 2941, 1515, 1463, 1261, 1156, 1029, 764

Reference Example 2

N,N-Bis(2-chloroethyl)-2-(3,4-dimethoxyphenyl) ethylamine hydrochloride (reference compound No. 2-1)

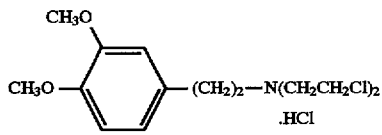

To a solution of N,N-bis(2-hydroxyethyl)-2-(3,4-dimethoxyphenyl)ethylamine (reference compound No. 1-1, 10.9 g) in chloroform (50 ml) was added thionyl chloride (14.4 g) dropwise under ice-cooling. The mixture was refluxed for 45 minutes. The reaction mixture was concentrated in vacuo, and isopropanol was added to the concentrate to give 10.2 g (74%) of the titled compound.

mp 147°–149° C.

IR (KBr, $cm^{-1}$) 2326, 1520, 1466, 1268, 1238, 1159, 1140, 1028

The following compound was prepared in the similar manner to Reference Example 2.
N,N-Bis(2-chloroethyl)-3-(3,4-dimethoxyphenyl) propylamine hydrochloride (reference compound No. 2-2)

mp 112°–123° C. (ethyl acetate-isopropyl ether)

IR (KBr, $cm^{-1}$) 2394, 1519, 1471, 1263, 1234, 1157, 1138, 1025

Reference Example 3

N,N-Bis(2-hydroxyethyl)-2-phenylethylamine (reference compound No. 3-1)

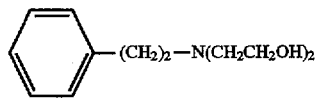

To a solution of 2-phenylethylbromide (20 g) in ethanol (100 ml) were added N,N-bis(2-hydroxyethyl)amine (90.8 g) and sodium iodide (21.6 g). The mixture was refluxed for 3 hours. The reaction mixture was concentrated in vacuo, saturated aqueous solution of sodium bicarbonate was added to the concentrate, and the whole was extracted with chloroform. The organic layer was washed with a saturated sodium chloride solution, dried over anhydrous magnesium sulfate, and concentrated in vacuo to give 17.5 g (77%) of the titled compound.

IR (film, $cm^{-1}$) 3382, 3026, 2947, 1495, 1455, 1047, 747, 700

The following compounds were prepared in the similar manner to Reference Example 3.
N,N-Bis(2-hydroxyethyl)-3-phenylpropylamine (reference compound No. 3-2)

IR (film, $cm^{-1}$) 3373, 2943, 1496, 1454, 1031, 749, 700
N,N-Bis(2-hydroxyethyl)-4-phenylbutylamine (reference compound No. 3-3)

IR (film, $cm^{-1}$) 3377, 2936, 1496, 1454, 1041, 748, 700
N,N-Bis(2-hydroxyethyl)-5-phenylpentylamine (reference compound No. 3-4)

IR (film, $cm^{-1}$) 3378, 2934, 1495, 1453, 1043, 747, 699

Reference Example 4

N,N-Bis(2-chloroethyl)-2-phenylethylamine hydrochloride (reference compound No. 4-1)

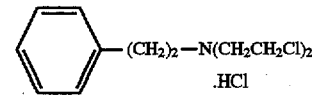

To a solution of N,N-bis(2-hydroxyethyl)-2-phenylethylamine (reference compound No. 3-1, 33.5 g) in chloroform (160 ml) was added thionyl chloride (57.1 g) dropwise under ice-cooling while stirring. The mixture was stirred at room temperature for 10 minutes, and refluxed for 1 hour. The reaction mixture was concentrated in vacuo, ethyl acetate and isopropyl ether were added to the concentrate, and the obtained crystals were collected by filtration to give 39.2 g (87%) of the titled compound.

mp 116°–117° C. (ethyl acetate-isopropyl ether)

IR (KBr, $cm^{-1}$) 3008, 2423, 1498, 1479, 1456, 766, 746, 704

The following compounds were prepared in the similar manner to Reference Example 4.

N,N-Bis(2-chloroethyl)-3-phenylpropylamine hydrochloride (reference compound No. 4-2)
mp 98°–100 °C. (ethyl acetate-isopropyl ether)
IR (KBr, cm$^{-1}$) 2965, 2360, 1484, 1458, 1325, 936, 753, 696

N,N-Bis(2-chloroethyl)-4-phenylbutylamine hydrochloride (reference compound No. 4-3)
mp 100°–112° C. (ethyl acetate-isopropyl ether)
IR (KBr, cm$^{-1}$) 2945, 2459, 1487, 1444, 1420, 926, 741, 698

N,N-Bis(2-chloroethyl)-5-phenylpentylamine hydrochloride (reference compound No. 4-4)
mp 69°–75° C. (ethyl acetate-isopropyl ether)
IR (KBr, cm$^{-1}$) 2937, 2859, 2459, 1454, 901, 742, 695

EXAMPLES

Example 1

1-[2-(3,4-Dimethoxyphenyl)ethyl]-4-(3-phenylpropyl) piperazine dihydrochloride (compound No. 1-1)

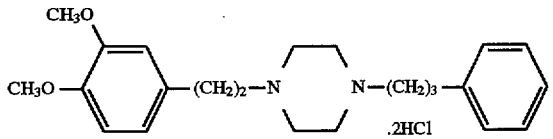

To a solution of N,N-bis(2-chloroethyl)-2-(3,4-dimethoxyphenyl)ethylamine hydrochloride (reference compound No. 2-1, 0.69 g) and 3-phenylpropylamine (0.41 g) in dimethylformamide (20 ml) were added potassium carbonate (0.83 g) and sodium iodide (0.90 g). The mixture was stirred at 70° C. for 2 hours. To the reaction mixture, water was added, and the whole was extracted with ethyl acetate. The organic layer was washed with water and a saturated sodium chloride solution, dried over anhydrous magnesium sulfate, and concentrated in vacuo. The oily residue was dissolved in ethanol, 6N hydrochloric acid (2 ml) was added thereto, and the solution was concentrated in vacuo to give 0.68 g (77%) of the titled compound (compound No. 1-1).
mp 258°–260° C. (decomp.)
IR (KBr, cm$^{-1}$) 3977, 2355, 1518, 1265, 1140, 1028, 754, 704

The following compounds were prepared in the similar manner to Example 1

1-[2-(3,4-Dimethoxyphenyl)ethyl]-4-(2-phenylethyl) piperazine dihydrochloride (compound No. 1-2)
mp 268°–272° C. (decomp.)
IR (KBr, cm$^{-1}$) 3430, 2938, 2300, 1519, 1447, 1264, 1234, 1026

1-[2-(3,4-Dimethoxyphenyl)ethyl]-4-benzylpiperazine dihydrochloride (compound No. 1-3)
mp 250°–253° C. (decomp.)
IR (KBr, cm$^{-1}$) 2978, 2360, 1520, 1467, 1267, 1236, 1149, 1027

1-[2-(3,4-Dimethoxyphenyl)ethyl]-4-(4-phenylbutyl) piperazine dihydrochloride (compound No. 1-4)
mp over 280° C. (ethanol)
IR (KBr, cm$^{-1}$) 2361, 1522, 1469, 1445, 1264, 1162, 1027, 696

1-[3-(3,4-Dimethoxyphenyl)propyl]-4-(2-phenylethyl) piperazine dihydrochloride (compound No. 1-5)
mp 254° C. (decomp., ethanol)
IR (KBr, cm$^{-1}$) 2360, 1518, 1455, 1236, 1139, 1028, 754, 703

1-[3-(3,4-Dimethoxyphenyl)propyl]-4-(3-phenylpropyl) piperazine dihydrochloride (compound No. 1-6)
mp 254°–257° C. (decomp., methanol)
IR (KBr, cm$^{-1}$) 2984, 2394, 1515, 1452, 1258, 1235, 1155, 1029

1-[3-(3,4-Dimethoxyphenyl)propyl]-4-(4-phenylbutyl) piperazine dihydrochloride (compound No. 1-7)
mp 256°–259° C. (decomp., ethanol)
IR (KBr, cm$^{-1}$) 2377, 1514, 1451, 1258, 1234, 1156, 1029, 699

Example 2

1-(3,4-Dimethoxybenzyl)-4-(2-phenylethyl)piperazine dihydrochloride (compound No. 2-1)

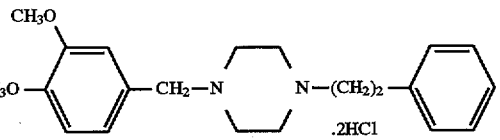

N,N-Bis(2-chloroethyl)-2-phenylethylamine hydrochloride (reference compound No. 4-1, 1.0 g), 3,4-dimethoxybenzylamine (1.2 g), potassium carbonate (1.5 g) and sodium iodide (1.1 g) were suspended in dimethylformamide (35 ml). This suspension was stirred at 30°–38° C. for 2.5 hours. To the reaction mixture, iced water was added, and the whole was extracted with ethyl acetate. The organic layer was washed with water and then with a saturated sodium chloride solution, dried over anhydrous sodium sulfate, and concentrated in vacuo. The oily residue was purified by silica gel column chromatography, and dissolved in methanol. To this methanol solution, conc. hydrochloric acid was added, and the precipitated crystals were collected by filtration to give 0.8 g (55%) of the titled compound.
mp ca. 280° C. (decomp.)
IR (KBr, cm$^{-1}$) 3447, 2980, 2335, 1590, 1520, 1449, 1265, 1245, 1159, 1022, 949, 914, 760, 701, 650

The following compounds were prepared in the similar manner to Example 2

1-(3,4-Dimethoxybenzyl)-4-(3-phenylpropyl)piperazine dihydrochloride (compound No. 2-2)
mp 257°–260° C. (decomp., ethanol)
IR (KBr, cm$^{-1}$) 2362, 1523, 1453, 1276, 1166, 1020, 750, 699

1-[2-(2,5-Dimethoxyphenyl)ethyl]-4-(3-phenylpropyl) piperazine dihydrochloride (compound No. 2-3)
mp 240° C. (decomp., ethanol)
IR (KBr, cm$^{-1}$) 2990, 2391, 1501, 1467, 1227, 1044, 959, 699

1-(3,4-Dimethoxybenzyl)-4-(4-phenylbutyl)piperazine dihydrochloride (compound No. 2-4)
mp 255° C. (decomp., ethanol)
IR (KBr, cm$^{-1}$) 2945, 2338, 1519, 1445, 1267, 1164, 1023, 761

1-[2-(3,4-Dimethoxyphenyl)ethyl]-4-(5-phenylpentyl) piperazine dihydrochloride (compound No. 2-5)
mp 260°–268° C. (decomp., ethanol)
IR (KBr, cm$^{-1}$) 2932, 2338, 1521, 1453, 1263, 1162, 1144, 700

Formulation Examples

Examples of the formulations of the compounds [I] according to this invention are shown below.

(Tablet)

| | |
|---|---|
| compound of this invention | 1 mg |
| lactose | 120 mg |
| crystalline cellulose | 38 mg |
| low substituted hydroxypropylcellulose | 5 mg |
| hydroxypropylcellulose-L | 5 mg |
| magnesium stearate | 1 mg |
| total | 170 mg |
| compound of this invention | 5 mg |
| lactose | 175 mg |
| crystalline cellulose | 68 mg |
| low substituted hydroxypropylcellulose | 10 mg |
| hydroxypropylcellulose-L | 10 mg |
| magnesium stearate | 2 mg |
| total | 270 mg |
| (Soft Capsule) | |
| compound of this invention | 50 mg |
| vegetable oil | 150 mg |
| gelatin coat | 140 mg |
| total | 340 mg |
| (Injection) | |
| compound of this invention | 100 mg |
| sodium chloride | 0.9 g |
| sodium hydroxide | q.s. |
| sterile purified water | q.s. |
| total | 100 ml |

EFFECT OF THE INVENTION

Pharmacological Test

1. In order to study the utility of the compounds of this invention, experiments were performed to examine affinities for sigma receptors.

1-1. Experiment Using [3H](+)-SKF-10047 as a Labeled Ligand

Affinities for sigma receptors were determined by the following method according to the report of Matsuno et al. (European Journal of Pharmacology, 231, 451–457 (1993)).

(Experimental Method)

A membrane preparation was prepared by the following method according to the paper of Tam et al. (Proc. Natl. Acad. Sci. USA, 80, 6703–6707 (1983)).

A brain of a Hartley guinea pig (weight: 300–400 g) was excised, the brain was homogenized in Tris-hydrochloric acid buffer (50 mM, pH 7.7, containing 0.32M sucrose) having a weight eight times that of the brain, and the homogenate was centrifuged to obtain a supernatant. The supernatant was ultracentrifuged for 20 minutes, the resulting pellet was suspended in Tris-hydrochloric acid buffer (50 mM, pH 7.7, the same buffer was used hereinafter), and the suspension was centrifuged again to obtain a membrane preparation.

The specific binding of $[^3H](+)$-SKF-10047 was determined by the following method in advance. To the membrane preparation suspended in Tris-hydrochloric acid buffer was added $[^3H](+)$-SKF-10047 (5 nM) dissolved in Tris-hydrochloric acid buffer without adding a test compound, and they were allowed to react at 25° C. for 30 minutes. Completing the reaction, the reaction mixture was filtered with suction through a glass filter, and radioactivity on the filter was measured with a liquid scintillation counter to determine total binding. In addition, to the membrane preparation was added a mixture of $[^3H](+)$-SKF-10047 (5 nM) and (+)-SKF-10047 (100 µM) having no radioactivity without adding the test compound, and the binding with the membrane preparation was determined in the same manner as described above. The obtained binding was defined as the non-specific binding. The difference between the total binding and the non-specific binding obtained in this manner was defined as the specific binding.

Secondly, the binding of the membrane preparation and $[^3H](+)$-SKF-10047 was measured in the presence of the test compound while varying the concentration of the test compound to determine the concentration of the test compound in which the specific binding of $[^3H](+)$-SKF-10047 determined previously is inhibited by 50%, i.e., $IC_{50}$.

(Result)

Results with compounds No. 1-1, 1-2 and 1-3 are shown in Table 1 as examples of the experimental results.

TABLE 1

| | $IC_{50}$ (nM) |
|---|---|
| compound No. 1-1 | 0.34 |
| compound No. 1-2 | 9.32 |
| compound No. 1-3 | 4.28 |

As shown in Table 1, the compounds of this invention were recognized to inhibit the specific binding of $[^3H](+)$-SKF-10047 remarkably in the low concentration, and the compounds were found out to have high affinities for sigma receptors.

1-2. Experiment Using $[^3H](+)$-PTZ as a Labeled Ligand

Affinities for sigma receptors were determined by the following method using $[^3H](+)$-PTZ as a labeled ligand according to the report of DeHaven-Hudkins et al. (Eur. I. Pharmacol., 227, 371–378 (1992)).

(Experimental Method)

A membrane preparation was prepared by the following method according to the paper of Tam et al. (Proc. Natl. Acad. Sci., USA, 80, 6703–6707 (1983)).

A brain of a Hartley guinea pig (weight: 300–400 g) was excised, the brain was homogenized in Tris-hydrochloric acid buffer (50 mM, pH 7.7, containing 0.32M sucrose) having a weight eight times that of the brain, and the homogenate was centrifuged to obtain a supernatant. The supernatant was ultracentrifuged for 20 minutes, the resulting pellet was suspended in Tris-hydrochloric acid buffer (50 mM, pH 7.7, the same buffer was used hereinafter), and the suspension was centrifuged again to obtain a membrane preparation.

The specific binding of $[^3H](+)$-PTZ was determined by the following method in advance. To the membrane preparation suspended in Tris-hydrochloric acid buffer was added $[^3H](+)$-PTZ (5 nM) dissolved in Tris-hydrochloric acid buffer without adding a test compound, and they were allowed to react at 37° C. for 150 minutes. Completing the reaction, the reaction mixture was filtered with suction through a glass filter, and radioactivity on the filter was measured with a liquid scintillation counter to determine total binding. In addition, to the membrane preparation was added a mixture of $[^3H](+)$-PTZ (5 nM) and (+)-PTZ (100 µM) having no radioactivity without adding the test compound, and the binding with the membrane preparation was determined in the same manner as described above. The obtained binding was defined as the non-specific binding. The difference between the total binding and the non-specific binding obtained in this manner was defined as the specific binding.

Secondly, the binding of the membrane preparation and $[^3H](+)$-PTZ was measured in the presence of the test compound while varying the concentration of the test compound to determine the concentration of the test compound in which the specific binding of [$^3$H](+)-PTZ determined previously is inhibited by 50%, i.e., IC$_{50}$.

(Result)

Results with compounds No. 1-1, 1-2, 1-4 and 1-6 are shown in Table 2 as examples of the experimental results. The results are expressed in averages of 4–11 samples.

TABLE 2

|  | IC$_{50}$ (nM) |
| --- | --- |
| compound No. 1-1 | 33.1 |
| compound No. 1-2 | 18.0 |
| compound No. 1-4 | 10.7 |
| compound No. 1-6 | 14.9 |

As shown in Table 2, the compounds of this invention were recognized to inhibit the specific binding of [$^3$H](+)-PTZ remarkably in the low concentration and to have high affinities for sigma receptors, as well as in examining [$^3$H](+)-SKF-10047 as a labeled ligand.

2. Experiment on the Increasing Effects on the Amount of Intracerebral Acetylcholine Since compounds increasing the amount of intracerebral acetylcholine were reported to be useful for therapeutic agents for dementia, etc. (The New England Journal of Medicine, 315, 1241–1245 (1986)), an experiment was performed to examine effects of the compounds of this invention on the amount of acetylcholine in rat brain.

(Experimental Method)

The amount of acetylcholine in rat brain was measured by the following method using intracerebral microdialysis method according to the report of Matsuno et al. (Brain Research, 575, 315–319 (1992)).

A probe was inserted in a brain of a male Wistar rat (weight: 280–300 g), Ringer's solution containing 3 μM eserine sulfate was perfused in the brain, acetylcholine recovered from the probe was determined by high-speed liquid chromatography. The amount of acetylcholine in rat brain was measured with time. When it became constant, the test compound suspended in 1% methylcellulose solution was administered orally to the rat, and the amount of intracerebral acetylcholine was measured. The amount of acetylcholine in rat brain (average of six samples) to which the test compound was not administered was used as a control. Table 3 shows the results expressed in percentages of amount of acetylcholine (averages of 3–7 samples in 30 minutes after administration of the test compound) to the control.

(Results)

TABLE 3

|  | amount of administration (mg/kg) | amount of acetylcholine (% control) |
| --- | --- | --- |
| compound No. 1-1 | 10 | 154.3 |
|  | 20 | 170.0 |
| compound No. 1-4 | 40 | 146.2 |
|  | 80 | 164.9 |
| compound No. 1-6 | 20 | 146.1 |
|  | 40 | 176.9 |

As shown in Table 3, the compounds of this invention were recognized to have excellent effects to increase the amount of intracerebral acetylcholine.

3. Experiment on Affinities for μ Receptors

Affinities for μ receptors were determined by the following method according to the report of Nabeshima et al. (Eur. J. Pharmacol., 114, 197–207 (1985)). As a [$^3$H]-labeled ligand of μ receptors, [$^3$H]DAMGO whose high selectivity of μ receptors had been reported was used (Br. J. Pharmac., 77, 461–469, (1982)).

(Experimental Method)

A membrane preparation was prepared by the following method according to the report of Kosterlitz et al. (Br. J. Pharmac., 68, 333–342 (1980)).

A brain of a male Wistar rat (weight: ca. 300 g) was excised, the brain was homogenized in Tris-hydrochloric acid buffer (50 mM, pH 7.7, the same buffer was used hereinafter) having a weight 20 times that of the brain, and the homogenate was ultracentrifuged for 15 minutes to obtain a pellet. This pellet was suspended in Tris-hydrochloric acid buffer, the suspension was incubated at 37° C. for 30 minutes, ultracentrifuged for 15 minutes, and the resulting pellet was used as a membrane preparation.

The specific binding of [$^3$H]DAMGO was determined by the following method in advance. To the membrane preparation suspended in Tris-hydrochloric acid buffer was added [$^3$H]DAMGO (1 nM) dissolved in Tris-hydrochloric acid buffer without adding a test compound, and they were allowed to react at 25° C. for 30 minutes. Completing the reaction, the reaction mixture was filtered with suction through a glass filter, and radioactivity on the filter was measured with a liquid scintillation counter to determine total binding. In addition, to the membrane preparation was added a mixture of [$^3$H]DAMGO (1 nM) and naloxone (5 μM) without adding the test compound, and the binding with the membrane preparation was determined in the same manner as described above. The binding was defined as the non-specific binding. The difference between the total binding and the non-specific binding obtained in this manner was defined as the specific binding.

Secondly, the binding of the membrane preparation and [$^3$H]DAMGO was measured in the presence of the test compound while varying the concentration of the test compound to determine the concentration of the test compound in which the specific binding of [$^3$H]DAMGO determined previously is inhibited by 50%, i.e., IC$_{50}$.

(Result)

Examples of the experimental results are shown below. Compounds No. 1-1, 1-2 and 1-3 exhibit IC$_{50}$ of higher than 10,000 nM, and the compounds of this invention were hardly recognized to inhibit the specific binding of [$^3$H]DAMGO. From these results, it turned out that affinities of the compounds of this invention for μ receptors are very low and that the compounds hardly exhibit morphine-like effects.

As apparent from the results of the above pharmacological tests, the compounds of this invention have high affinities for sigma receptors, hardly exhibit morphine-like effects, and have wide pharmaceutical uses for therapeutic agents for diseases in which sigma receptors are concerned, for example, cerebral neural function disorders such as dementia, depression, schizophrenia and anxiety neurosis, diseases accompanying abnormal immune response and cryptorrhea, digestive ulcer, etc. In addition, the compounds of this invention are particularly useful for therapeutic agents for cerebral neural function disorders coupled with increasing effects on the amount of intracerebral acetylcholine and improving effects on learning disorders caused by a cerebrovascular disorder.

INDUSTRIAL POSSIBILITY OF UTILIZATION

The compounds of this invention, that is, 1,4-(diphenylalkyl)piperazine derivatives have affinities for sigma receptors and are useful for therapeutic agents for cerebral neural function disorders such as dementia, depression, schizophrenia and anxiety neurosis, diseases accompanying abnormal immune response and cryptorrhea, digestive ulcer, etc.

What is claimed is:

1. A compound represented by the formula [I] or a salt thereof,

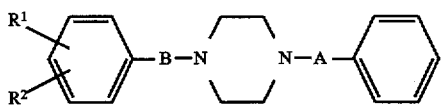

wherein $R^1$ and $R^2$ are the same or different and each represents a lower alkoxy group; A and B are the same or different and each represents a $C_2$-$C_4$ alkylene group.

2. The compound or a salt thereof as defined in claim 1 wherein A is —$(CH_2)_2$—, —$(CH_2)_3$— or —$(CH_2)_4$—.

3. The compound or a salt thereof as defined in claim 1 wherein B is —$(CH_2)_2$— or —$(CH_2)_3$—.

4. The compound or a salt thereof as defined in claim 1 wherein A is —$(CH_2)_3$— and B is —$(CH_2)_2$—.

5. The compound or a salt thereof as defined in claim 1 wherein each of A and B is —$(CH_2)_3$—.

6. The compound or a salt thereof as defined in claim 1 wherein each of A and B is —$(CH_2)_2$—.

7. The compound or a salt thereof as defined in claim 1 wherein A is —$(CH_2)_4$— and B is —$(CH_2)_2$—.

8. The compound or a salt thereof as defined in claim 1 wherein each of $R^1$ and $R^2$ is a methoxy group.

9. The compound or a salt thereof as defined in claim 1 wherein $R^1$ and $R^2$ are both methoxy groups and the compound is of the following formula:

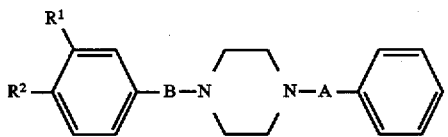

10. A compound represented by the formula [II] or a salt thereof

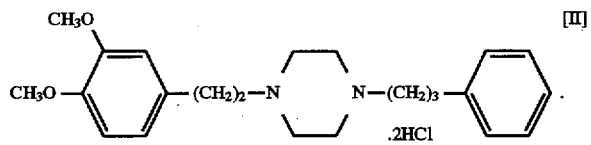

11. A compound represented by the formula [III] or a salt thereof

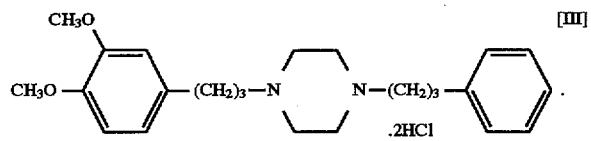

12. A therapeutic agent for treating a cerebral neural function disorder which comprises (a) a compound of the following formula or a salt thereof as an active ingredient:

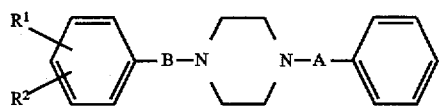

wherein $R^1$ and $R^2$ are the same or different and each represents a lower alkoxy group; A and B are the same or different and each represents a $C_2$-$C_4$ alkylene group, and (b) a diluent, lubricant, disintegrator, binder, coating agent or film forming agent.

13. The therapeutic agent for treating a cerebral neural function disorder as defined in claim 12 wherein A is —$(CH_2)_2$—, —$(CH_2)_3$— or —$(CH_2)_4$—.

14. The therapeutic agent for treating a cerebral neural function disorder as defined in claim 12 wherein B is —$(CH_2)_2$— or —$(CH_2)_3$—.

15. The therapeutic agent for treating a cerebral neural function disorder as defined in claim 12 wherein A is —$(CH_2)_3$— and B is —$(CH_2)_2$—.

16. The therapeutic agent for treating a cerebral neural function disorder as defined in claim 12 wherein each of A and B is —$(CH_2)_3$—.

17. The therapeutic agent for treating a cerebral neural function disorder as defined in claim 12 wherein each of A and B is —$(CH_2)_2$—.

18. The therapeutic agent for treating a cerebral neural function disorder as defined in claim 12 wherein A is —$(CH_2)_4$— and B is —$(CH_2)_2$—.

19. The therapeutic agent for treating a cerebral neural function disorder as defined in claim 12 wherein each of $R^1$ and $R^2$ is a methoxy group.

20. The therapeutic agent for treating a cerebral neural function disorder as defined in claim 12 wherein $R^1$ and $R^2$ are both methoxy groups and the compound is of the following formula:

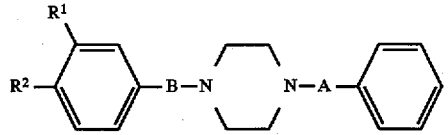

21. The therapeutic agent for treating a cerebral neural function disorder as defined in claim 12, wherein the compound is of the following formula:

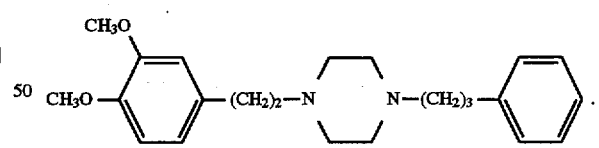

22. The therapeutic agent for treating a cerebral function disorder as defined in claim 12, wherein the compound is of the following formula:

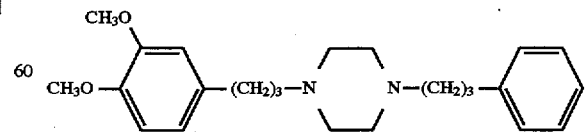

* * * * *